US00PP31970P2

(12) United States Plant Patent
LaBonte et al.

(10) Patent No.: US PP31,970 P2
(45) Date of Patent: Jul. 14, 2020

(54) SWEETPOTATO PLANT NAMED 'LA08-21P'

(50) Latin Name: ***Ipomoea batatas* (L.) Lam**
Varietal Denomination: LA08-21P

(71) Applicant: The Board of Supervisors of Louisiana State University and Agricultural and Mechanical College, Baton Rouge, LA (US)

(72) Inventors: Don R. LaBonte, Baton Rouge, LA (US); Arthur Q. Villordon, Chase, LA (US); Christopher A. Clark, Baton Rouge, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 16/350,984

(22) Filed: Feb. 8, 2019

(51) Int. Cl.
*A01H 5/06* (2018.01)
*A01H 6/00* (2018.01)

(52) U.S. Cl.
USPC ..... Plt./258

(58) Field of Classification Search
USPC ..... Plt./258, 263.1, 226, 256
CPC ... A01H 5/06; A01H 5/02; A01H 5/12; A01H 5/00; A01H 5/04; A01H 6/00
See application file for complete search history.

(56) References Cited

U.S. PATENT DOCUMENTS

PP15,038 P3 * 7/2004 LaBonte ..... A01H 5/04 Plt./258

* cited by examiner

*Primary Examiner* — June Hwu
(74) *Attorney, Agent, or Firm* — Baker Donelson

(57) ABSTRACT

A new variety of sweetpotato, identified as 'LA08-21P', is disclosed having resistance to both *Fusarium* wilt and southern root knot nematode; a light purple-banded flesh and deep-purple skin, and moderately high yield characteristics.

3 Drawing Sheets

Genus and species name: *Ipomoea batatas* (L.) Lam.
Variety denomination: 'LA08-21P'.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

This new and distinct sweetpotato variety demonstrates superior disease resistance to *fusarium* wilt and exhibits a storage root with light purple banded flesh. It also demonstrates a deep purple skin in comparison to '05-111' with a light to medium rose skin.

This new and distinct sweetpotato variety is identified as 'LA08-21P' and is characterized by a storage root with light purple-banded flesh, consistent shape, and a deep purple skin.

DETAILED BOTANICAL DESCRIPTION

This new variety of sweetpotato, named 'LA08-21P', resulted from an open-pollinated cross performed in 2007 to the patented female parent 'Evangeline' (U.S. Plant Pat. No. 19,710 P3). The male parent was unknown. Two patented male parents ('05-111' patented U.S. Plant Pat. No. 23,761 P3; 'L96-117' patented U.S. Plant Pat. No. 15,038 P3) were among the potential pollen sources in the crossing nursery. 'LA08-21P' was developed to provide a variety with characteristics similar to '05-111', but with a deep purple skin and light purple-banded flesh. The female parent 'Evangeline' has orange fleshed storage roots.

Plants of 'LA08-21P' and variety '05-111' can be differentiated. Abaxial (medium intensity) and adaxial veins (small intensity) of 'LA08-21P' are dark purple [10 R (red) P (purple) (2/4)]. '05-111' has no purple hue to veins. Roots of 'LA08-21P' are a deep purple skin and can be differentiated from the light rose skin of the female parent 'Evangeline' (U.S. Plant Pat. No. 19,710 P3). Color terminology used herein is in accordance with the MUNSELL® Book of Color (2003 Edition, Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'LA08-21P'.

'LA08-21P' roots were stored during the winter in Chase, La. 'LA08-21P' was planted the following spring, resulting in approximately 8-10 sprouts per root. Cuttings from the sprouts were transplanted successfully for asexual reproduction in Chase, La. Asexual propagation of the new cultivar by cuttings has shown that the unique features of this new sweetpotato were stable and that the plant reproduced true to type in successive generations of asexual propagation. Plants described herein were 90 days in age from planting in full sun field plantings.

Figure 1:
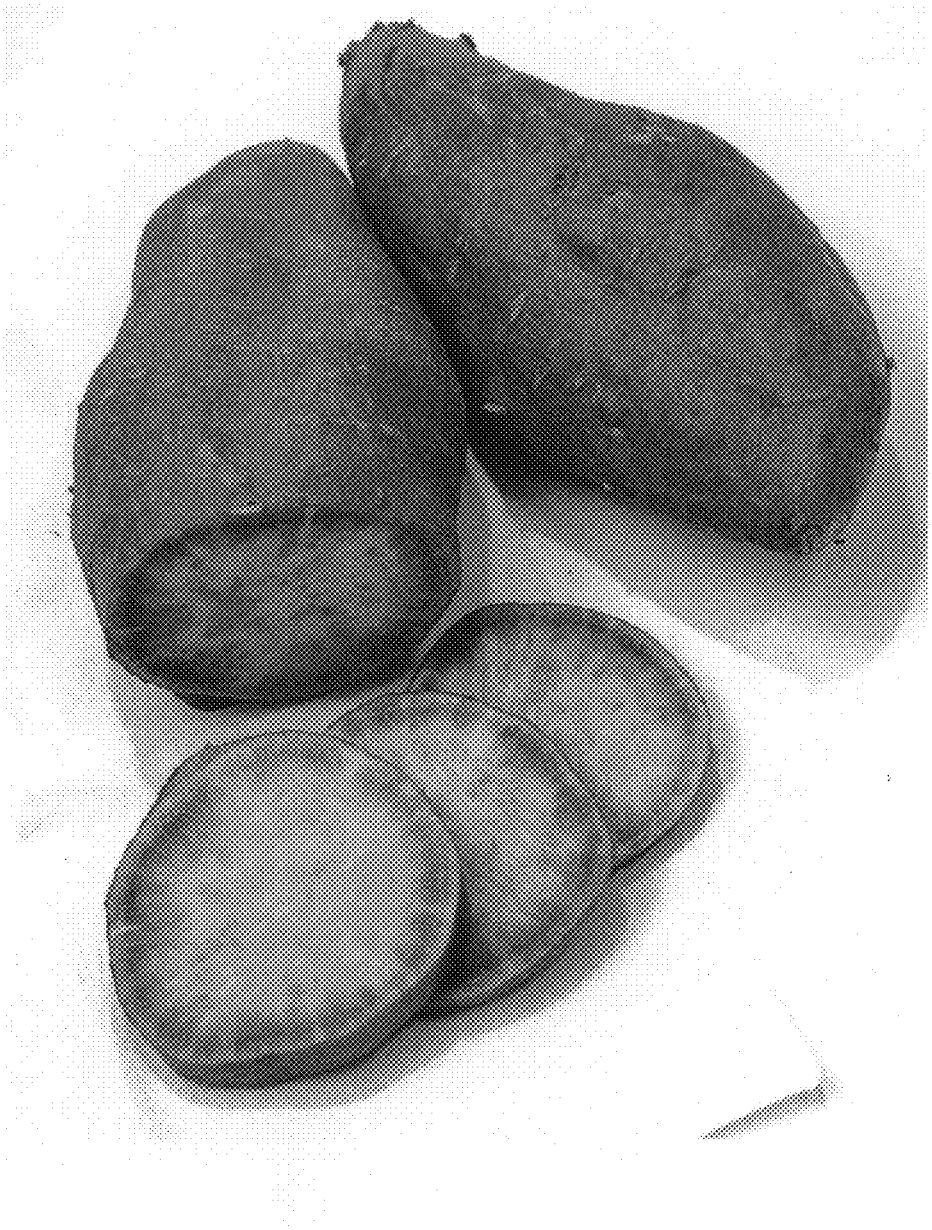
FIG. 1 is a color photograph of the fleshy root form of the novel variety of sweetpotato identified as 'LA08-21P'.
Figure 2:
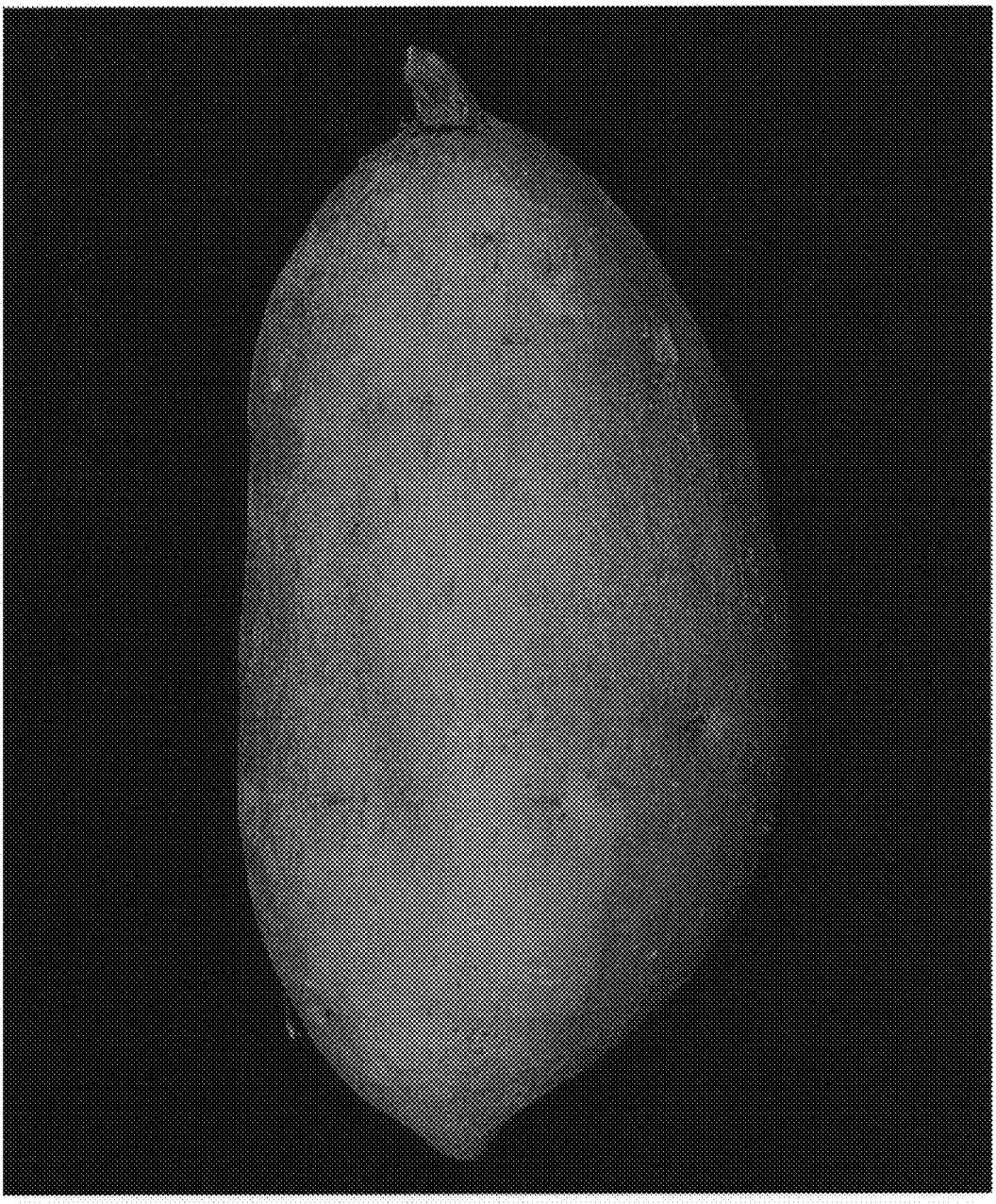
FIG. 2 is a color photograph of the fleshy root form of the sweetpotato variety identified as '05-111'.

FIG. 1 depicts the fleshy root form of the 'LA08-21P' sweetpotato. The skin is a deep purple and differs from the light to medium rose '05-111', both at harvest and after several months of storage as shown in Table 1. No eyes or lateral grooving is present. MUNSELL® Book of Color values for skin and flesh for both 'LA08-21P' and '05-111' storage roots are shown in Table 1. The '05-111' sweetpotato is depicted in FIG. 2. The skin for both 'LA08-21P' and '05-111' was smooth. The 'LA08-21P' cortex was 3.3 mm in depth and the color is similar throughout. The flesh of 'LA08-21P' is pink-white (background) with purple bands in comparison to the orange flesh of '05-111'. Storage root shape for 'LA08-21P' is oblong. There is greater production of small caliber storage roots consistent with a Canner (25-51 mm in diameter, 51-178 mm long) grade.

TABLE 1

| Variable | Variety | Color |
|---|---|---|
| Skin | 'LA08-21P' | 7.5 R (red) P (purple) 3/4 |
| | '05-111' | 2.5 Y (yellow) R (red) 6/6 |
| Flesh | 'LA08-21P' | background-2.5 R (red) P (purple) 9/2<br>bands-7.5 R (red) P (purple) 3/4 |
| | '05-111' | 2.5 Y (yellow) R (red) 7/8 |

Figure 3:
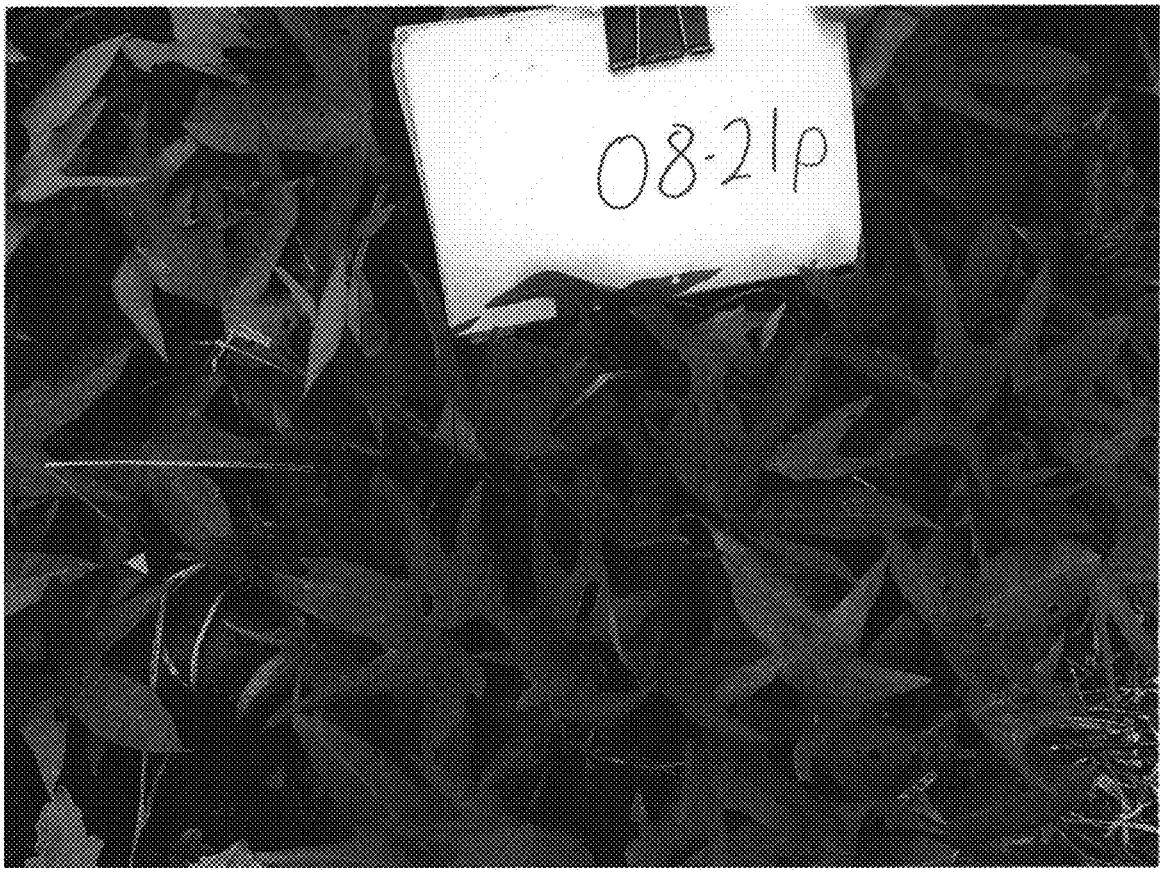
FIG. 3 is a color photograph of the canopy biomass designated as 08-21P in the photograph of the novel variety of sweetpotato identified as 'LA08-21P'.

FIG. 3 depicts the canopy biomass of 'LA08-21P' sweetpotato. 'LA08-21P' has glabrous, green apical tips [2.5 G (green) Y (yellow) (7/8)] and vines change to purple [2.5 R (red) P (purple) (2/6)] 18 cm from the apex and extends to the crown of the roots. 'LA08-21P' canopy biomass appears similar to '05-111'. The 'LA08-21P' canopy architecture was 15 cm in height from the soil surface and semi-upright. For 'LA08-21P', three to four main vines arose from the main stem near the soil surface. The stem giving rise to these vines was 1.7 cm in diameter; the 3-4 lateral vines were 107 cm in length with diameters of about 0.8 cm at 65 cm from the base and diameters of about 0.3 cm at the first internode of the first fully developed leaf from the apex; the average spread is 100 cm from the root crown. Two lateral branches arose from each of the main vines. At the first internode from the apex, the internode length was about 1.9 cm between the first and second fully developed leaves. Internode lengths for other sections of the vine averaged about 2.2 cm. The youngest unfolded immature leaves at the apex were green [5 G (green) Y (yellow) (4/4)] for the adaxial and abaxial surface, which change quickly over one to two nodes from the apex for the adaxial surface to a purple [10 P (purple) (2/4)] mottled dark green [5 G (green) Y (yellow) (3/4)]. Anthocyanin coloration is weak and pubescence absent for stem tips. The abaxial surface of young leaves are similar except more red than purple [10 R (red) P (purple) 2/4] and lighter green mottle [5 G (green) Y (yellow) (5/4)]. These characteristics represent the first 2-3 open leaves. Mature leaves quickly become green [7.5 G (green) Y (yellow) (3/4)]. Mature leaves at five nodes from the apex have 5 deep lobes, a cordate base, and an entire leaf margin. Mature leaves were about 10.5 cm long and 11.5 cm wide. Leaves were glabrous, smooth texture, without undulations on adaxial and abaxial surfaces, slightly drooping, and pliable. Adaxial and abaxial veins were in a pinnate venation pattern and purple [10 R (red) P (purple) (2/4)] and incrementally fade to lighter green [5 G (green) Y (yellow) (5/4)] near the tip of leaves for the adaxial surface and to a lesser extent on the abaxial surface. The petiole was purple [10 R (red) P (purple) (2/4)] as well as the base of the petiole with the leaf junction on both abaxial and adaxial surfaces. The petiole was 10.5 cm long at five nodes from the apex, and 2.5 mm in diameter at 5 cm from the leaf junction. The dormant nodal meristem was purple [10 R (red) P (purple) (2/4)].

A typical inflorescence of 'LA08-21P' displayed one cluster of three-five flowers per peduncle. Peduncles were dark purple [10 P (purple) (2/4)], about 13-14 cm long, and about 3 mm in diameter. Individual flowers were about 4.3 cm long from the base of the calyx, and the corolla was 3 cm wide at the opening. The fused flower petals formed a pentagonal pattern with smooth edges. The inner throat of the corolla was purple [7.5 P (purple) (3/6)]. The inner and outer limbs of the corolla (corollas outermost area, distal from the calyx) were light purple [7.5 P (purple) (8/6)]. The five sepals comprising the calyx were elliptic with a cordate apex and green [2.5 G (green) Y (yellow) (5/6)] and translucent; three of these sepals were about 12 mm long and 5 mm wide. Two other sepals (interspersed) were about 7 mm long and 2 mm wide. Sepal margins were entire; these sepals had a purple hue [7.5 P (purple) (2/6)]. Stigmata were about 1.7 cm long and purple [7.5R (red) P (purple) (8/6)] at the base before fading. Five stamens were inferior to the stigmata. No fragrance was present. Mature seed capsules are round and 6.3 mm in length and width, and seeds are 3.5 mm round. One black [neutral 1.75] seed is produced on average per capsule.

EXAMPLE 1

Tests Conducted

To confirm that 'LA08-21P' was a new variety, controlled tests (e.g., pathogen responses and yield) were conducted in Baton Rouge, La. '05-111' was selected for comparison because of its importance in commercial United States orange flesh sweetpotato acreage. Diseases that commonly affect the growth of sweetpotatoes were selected to test for pathogen responses in both varieties. Scions of 'LA08-21P' and '05-111' reacted similarly to most diseases evaluated in the controlled tests. 'LA08-21P' and '05-111' were intermediate to resistant for *Streptomyces* soil rot caused by *Streptomyces ipomoeae* (Person & W. J. Martin) Waksman & Henrici. 'LA08-21P' was intermediate to resistant and '05-111' was resistant to *Fusarium* wilt or stem rot caused by *Fusarium oxysporum* Schlect. f sp. *batatas* (Wollenw.) Snyd. & Hans. 'LA08-21P' was susceptible and '05-111' was resistant to *Rhizopus* soft rot caused by *Rhizopus stolonifer* (Ehr. ex. Fr.) Lind. 'LA08-21P' was resistant and '05-111' was susceptible to bacterial root rot caused by *Dickeya dadantii* Samson et al. as measured by postharvest inoculation of storage roots.

Nematode reproduction was measured in greenhouse tests. 'LA08-21P' was resistant while '05-111' was susceptible to race 3 of the southern root-knot nematode, *Meloidogyne incognita* (Kofoid & White 1919) Chitwood 1949.

'LA08-21P' has not been tested for novel insect resistance.

'LA08-21P' is drought and heat tolerant like '05-111' and succumbs to death at freezing like '05-111'.

To determine yield production, complete-block trials using three to four replications of '05-111' and 'LA08-21P' each were conducted in 2011, 2013, and 2017 in areas of Louisiana, Arkansas, and Alabama. 'LA08-21P' and '05-111' sweetpotato plants were transplanted in randomized complete-block trials at 31 cm spacings. Each block/plot was fertilized with approximately 250 pounds per acre of a mixed fertilizer comprising 13% N, 13% $P_2O_5$, and 13% $K_2O$. '05-111' was compared to 'Beauregard' at transplanting dates beginning in May-July. Average yields were measured for the following grades of roots: U.S. #1 (51-89 mm in diameter, 76-229 mm long); Canner (25-51 mm in diameter, 51-178 mm long); and Jumbo (larger than U.S. #1 in diameter, length or both, and without objectionable defects). A typical marketable root of '05-111' was 180-190 mm long, 60-70 mm in diameter, with mostly round-elliptic to irregular in shapes. The base or distal end tended to be more elongated in comparison to slightly rounder apex (proximal end). U.S. #1 roots typically weighed 150-190 g.

A late-season transplanting date trial was conducted at Gilbert, La. in 2017. 'LA08-21P' and '05-111' were transplanted on Jul. 20, 2017 and harvested on Nov. 16, 2017 (119 days after planting). Average yields, measured as Metric Tons per Hectare ($MT \cdot ha^{-1}$), by grade of 'LA08-21P' and '05-111' are shown in Table 2.

TABLE 2

Late-season transplant date yield trial.

| Selection | US#1† | Canners† | Jumbos† | TMY‡† |
|---|---|---|---|---|
| 'LA08-21P' | 17.09a | 9.75a | 5.38a | 32.22a |
| '05-111' | 16.08a | 7.79a | 2.47a | 26.33a |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Wynne, Ark. in 2017. 'LA08-21P' and '05-111' were transplanted on Jun. 6, 2017 and harvested on Oct. 26, 2017 (121 days after planting). Average yields, measured as Metric Tons per Hectare ($MT \cdot ha^{-1}$), by grade of 'LA08-21P' and '05-111' are shown in Table 3.

TABLE 3

Mid-season transplant date yield trial.

| Selection | US#1† | Canners† | Jumbos† | TMY‡† |
|---|---|---|---|---|
| 'LA08-21P' | 14.62b | 20.79a | 5.38a | 40.85b |
| '05-111' | 24.42a | 10.81a | 26.22a | 61.41a |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Montrose, Ark. in 2013. 'LA08-21P' and '05-111' were transplanted on May 31, 2013 and harvested on Oct. 30, 2013 (153 days after planting). Average yields, measured as Metric Tons per Hectare ($MT \cdot ha^{-1}$), by grade of 'LA08-21P' and '05-111' are shown in Table 4.

TABLE 4

Mid-season transplant date yield trial.

| Selection | US#1† | Canners† | Jumbos† | TMY‡† |
|---|---|---|---|---|
| 'LA08-21P' | 25.16b | 12.33a | 0a | 37.54a |
| '05-111' | 52.39a | 15.69a | 0a | 77.32a |

†Average yields in $MT \cdot ha^{-1}$ of varieties followed by a common letter do not differ significantly ($P < 0.05$) according to Duncan's Multiple Range Test.
TMY‡ = total marketable yield A late-season transplanting date trial was also conducted at Wynne, Ark. in 2013. 'LA08-21P' and '05-111' were transplanted on Jun. 21, 2013 and harvested on Oct. 28, 2013 (130 days after planting). Average yields measured as Metric Tons per Hectare ($MT \cdot ha^{-1}$) by grade of 'LA08-21P' and '05-111' are shown in Table 5.

TABLE 5

Late-season transplant date yield trial.

| Selection | US#1† | Canners† | Jumbos† | TMY‡† |
|---|---|---|---|---|
| 'LA08-21P' | 10.20b | 28.52a | 0a | 38.72a |
| '05-111' | 31.66a | 11.04a | 3.08a | 45.78a |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Elberta, Ala. in 2011. 'LA08-21P' and '05-111' were transplanted on Jun. 3, 2011 and harvested on Sep. 22, 2011 (112 days after planting). Average yields measured as Metric Tons per Hectare ($MT \cdot ha^{-1}$) by grade of 'LA08-21P' and '05-111' are shown in Table 6.

TABLE 6

Mid-season transplant date yield trial.

| Selection | US#1† | Canners† | Jumbos† | TMY‡† |
|---|---|---|---|---|
| 'LA08-21P' | 11.71a | 11.2a | 0a | 22.92a |
| '05-111' | 16.08a | 11.2a | 2.80a | 30.20a |

†Average yields in $MT \cdot ha^{-1}$ of varieties followed by a common letter do not differ significantly ($P < 0.05$) according to Duncan's Multiple Range Test.
TMY‡ = total marketable yield As shown in Tables 2-6, 'LA08-21P' produced yields less than '05-111' in regional trials at various planting dates for the U.S. #1 grade. Yield for the canner grade was similar and often higher in comparison to '05-111'. Yield declines are within norms in poor environments. 'LA08-21P' had harvestable roots approximately 115-120 days after planting, which is typical development time for sweetpotatoes and comparable to '05-111'. The yield of Jumbo grade is indicative of earliness and 'LA08-21P' had fewer jumbos in comparison to '05-111'. In total, this data reflects lower yield (~25%) for the combined U.S. #1 and canner grade. Markets are accepting of smaller purple flesh varieties and thus salable quantities are produced. 'LA08-21P' has a storage life and shipping quality comparable to '05-111P'.

'LA08-21P' should be a valuable commercial sweetpotato variety. 'LA08-21P' represents a novel flesh and skin color useful in marketing as a specialty type deep purple skin with light purple banded flesh.

We claim:

1. A new and distinct variety of *Ipomoea batatas* plant named 'LA08-21P' as described and illustrated in the specification herein.

* * * * *